US00PP30847P3

(12) United States Plant Patent
Cerny et al.

(10) Patent No.: US PP30,847 P3
(45) Date of Patent: Aug. 27, 2019

(54) APPLE TREE NAMED 'UEB 43054'

(50) Latin Name: ***Malus domestica* (Borkh.)**
Varietal Denomination: UEB 43054

(71) Applicant: Institute of Experimental Botany AS CR, v.v.i. (UEB), Prague (CZ)

(72) Inventors: Radek Cerny, Ricany u Prahy (CZ); Jan Zima, Turnov (CZ); Otto Louda, Pencin u Liberce (CZ); Jaroslav Tupy, Prague (CZ)

(73) Assignee: Institute of Experimental Botany AS CR, v.v.i. (UEB), Prague (CZ)

( * ) Notice: Subject to any disclaimer, the term of this patent is extended or adjusted under 35 U.S.C. 154(b) by 0 days.

(21) Appl. No.: 15/932,496

(22) Filed: Mar. 7, 2018

(65) Prior Publication Data

US 2018/0263153 P1 Sep. 13, 2018

Related U.S. Application Data

(60) Provisional application No. 62/600,978, filed on Mar. 8, 2017.

(51) Int. Cl.
*A01H 5/08* (2018.01)
*A01H 6/74* (2018.01)

(52) U.S. Cl.
USPC ..... Plt./161
CPC ..... *A01H 6/7418* (2018.05)

(58) Field of Classification Search
USPC ..... Plt./161, 175
See application file for complete search history.

*Primary Examiner* — Susan McCormick Ewoldt
(74) *Attorney, Agent, or Firm* — The Webb Law Firm

(57) ABSTRACT

A new and distinct *Malus domestica* (Borkh.) late ripening, dessert variety that exhibits a columnar tree growth type, very narrow growth habit, $V_f$-resistance against scab, and bright red fruits having good taste and storability. The new variety is suitable for home apple growing as solitary trees or in groups to function as hedges. The new variety is also suitable for commercial apple production for the juice industry.

10 Drawing Sheets

Botanical classification: *Malus domestica* (Borkh.).
Varietal denomination: 'UEB 43054'.

BACKGROUND OF THE INVENTION

The present invention comprises a new and distinct cultivar of apple tree botanically classified as *Malus domestica* (Borkh.) and known by the varietal name 'UEB 43054'.

The new variety is the result of a cross in a planned breeding program between 'Red Topaz' (female parent, U.S. Plant Pat. No. 18,895) and 'Rondo' (male parent, unpatented). The cross resulting in 'UEB 43054' occurred in the Spring of 2004 at 310 meters above sea level with a mean annual temperature of 7.7° C. and a mean annual precipitation of 680 mm. The purpose of the breeding program was to develop an apple variety having red colored fruits with a columnar tree growth type that exhibits $V_f$-resistance against scab. The new variety was discovered in 2009 with the first flowering and fruiting of the original seedling in the Czech Republic. Subsequently, the new variety was asexually reproduced in Pencin u Liberce in the Czech Republic by budding/grafting on apple rootstocks in the Spring of 2010.

The new variety is similar to its female parent, 'Red Topaz', in exhibiting obloid-shaped fruits with a small height/diameter ratio, large area of overcolor, medium to late time of eating maturity and $V_f$-resistance against scab. However, 'UEB 43054' exhibits a columnar tree growth type, a short fruit stalk, and leaves of medium to long length, while 'Red Topaz' exhibits a ramified tree growth type, a medium fruit stalk, and leaves of short to medium length. The new variety is similar to its male parent, 'Rondo', in exhibiting weak tree vigor, a red hue of overcolor, and $V_f$-resistance against scab. However, 'UEB 43054' exhibits a large area of solid overcolor and yellow fruit ground color, while 'Rondo' exhibits a medium area of solid overcolor with weakly defined stripes and a green-yellow fruit ground color.

Further, when compared to apple tree named 'UEB 41811' (U.S. Plant patent application Ser. No. 15/932,495, concurrently applied-for herewith), both varieties exhibit a columnar tree growth type and $V_f$-resistance against scab. However, the fruits of 'UEB 43054' exhibit a red hue of overcolor while the fruits of 'UEB 41811' exhibit a yellow hue of overcolor.

The following characteristics also distinguish the new variety from other varieties known to the breeders:

- Medium to late ripening;
- Columnar tree growth type with a very narrow growth habit;
- Weak tree vigor;
- Early time to beginning of flowering;
- Fruit shape is obloid with a small height/diameter ratio;
- Solid flush overcolor having a red hue;
- Short fruit stems of medium thickness;
- Medium to late harvesting and time of eating maturity; and
- Resistance against scab on $V_f$-gene basis.

The new variety has been trial and field tested and has been found to retain its distinctive characteristics and remain true to type through successive asexual propagations.

DESCRIPTION OF THE DRAWINGS

The accompanying photographic drawings illustrate the new cultivar taken of/from a tree at approximately 6 years of age, except where indicated below, with the color being as nearly true as possible with color illustrations of this type. It should be noted that colors may vary with growing conditions and time of year.

DESCRIPTION OF THE PLANT

Figure 1:
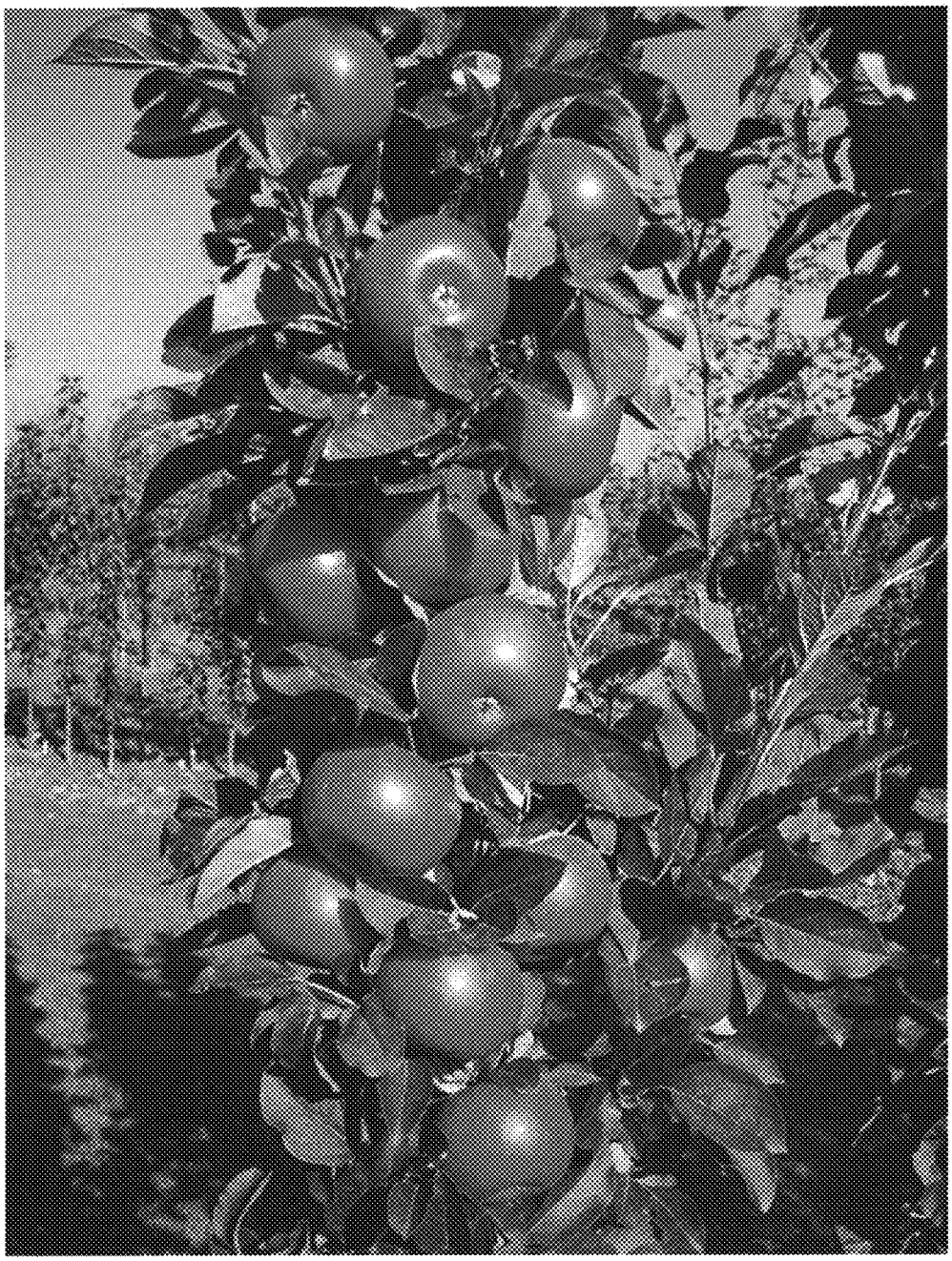
FIG. 1 illustrates details of fruits of the new variety at picking maturity.
Figure 2:
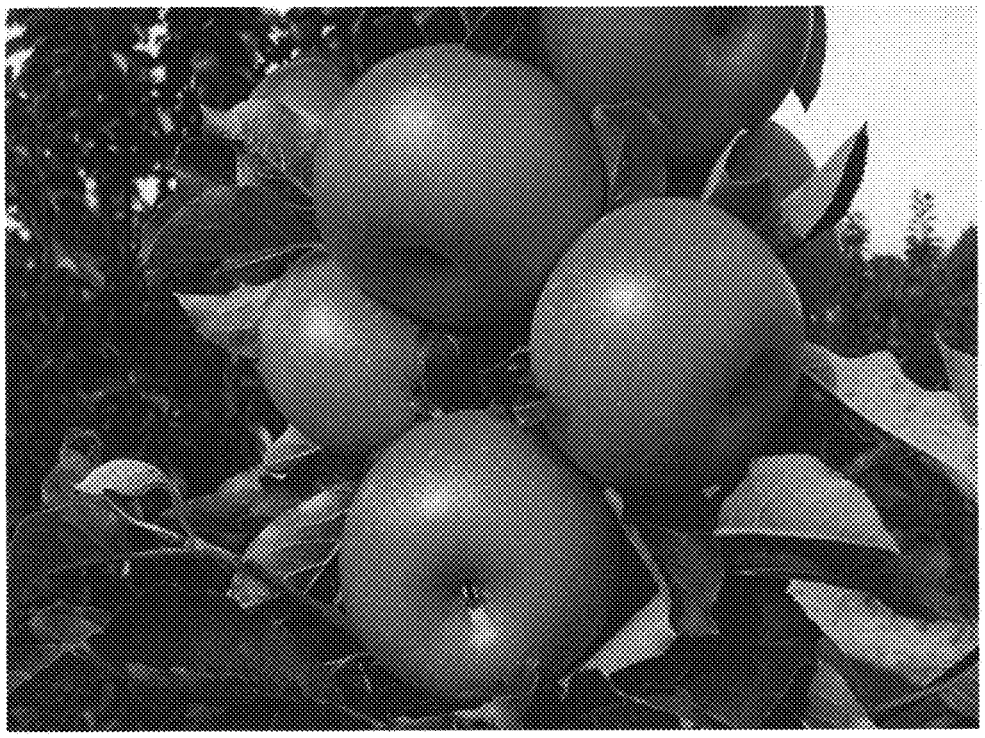
FIG. 2 illustrates details of fruits of the new variety at picking maturity.
Figure 3:
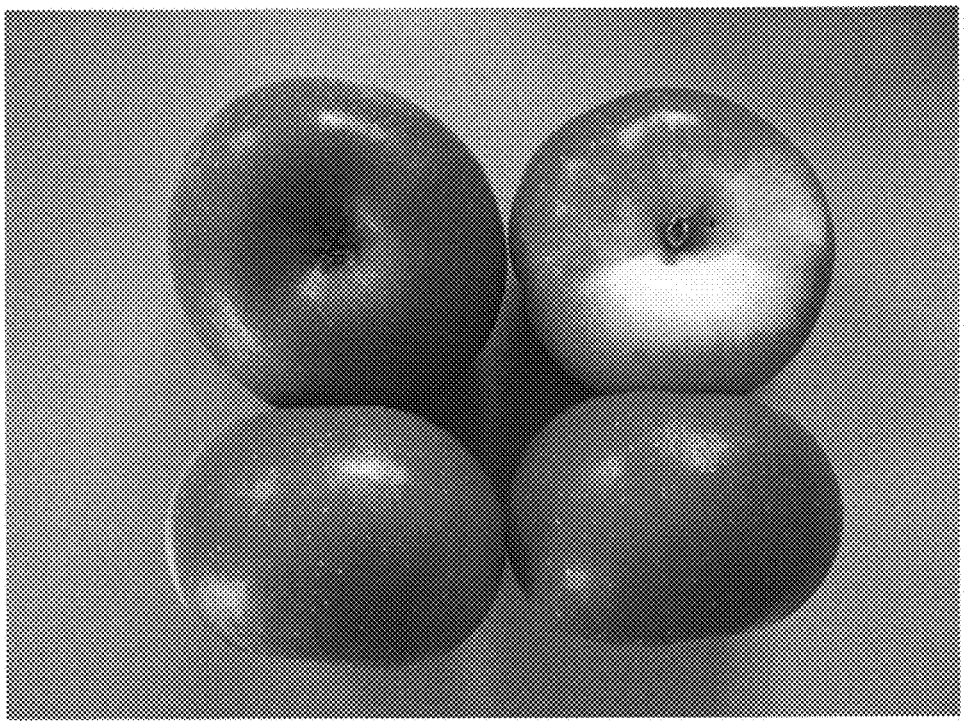
FIG. 3 illustrates details of fruits of the new variety at eating maturity.
Figure 4:
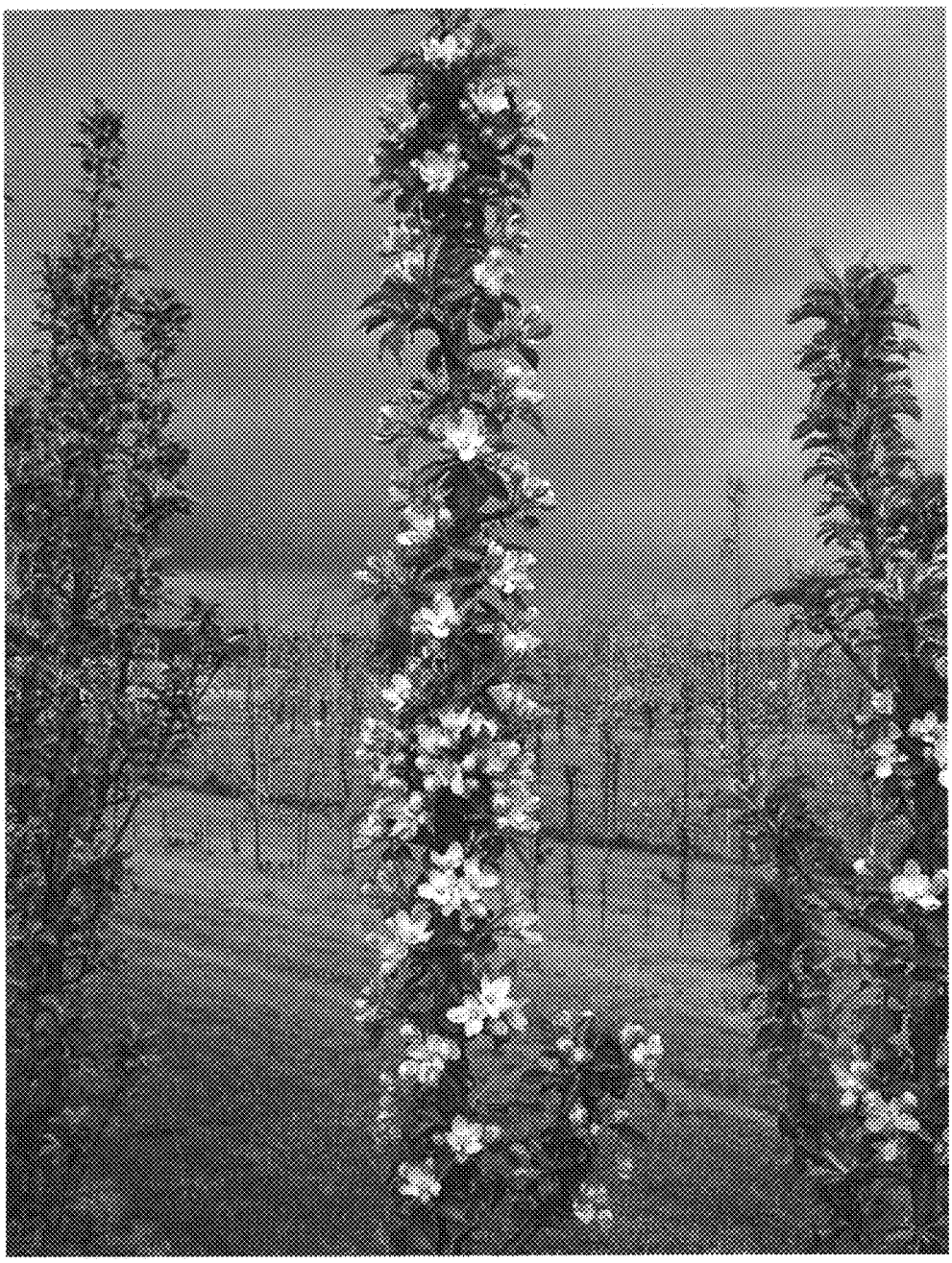
FIG. 4 illustrates the original tree of the new variety, showing its canopy form at blossoming time.
Figure 5:
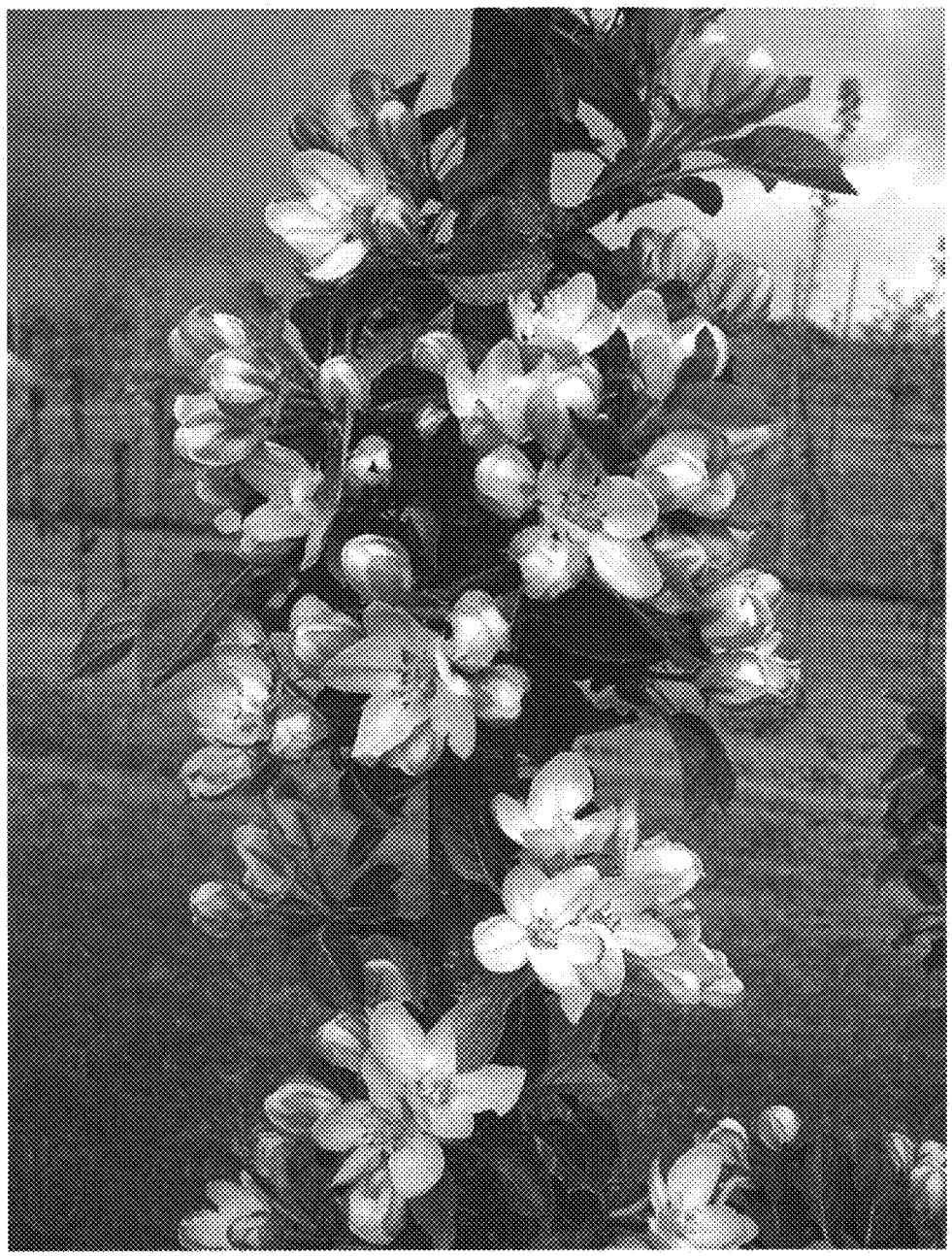
FIG. 5 illustrates details of blossoms of the new variety at the beginning of blossoming time.
Figure 6:
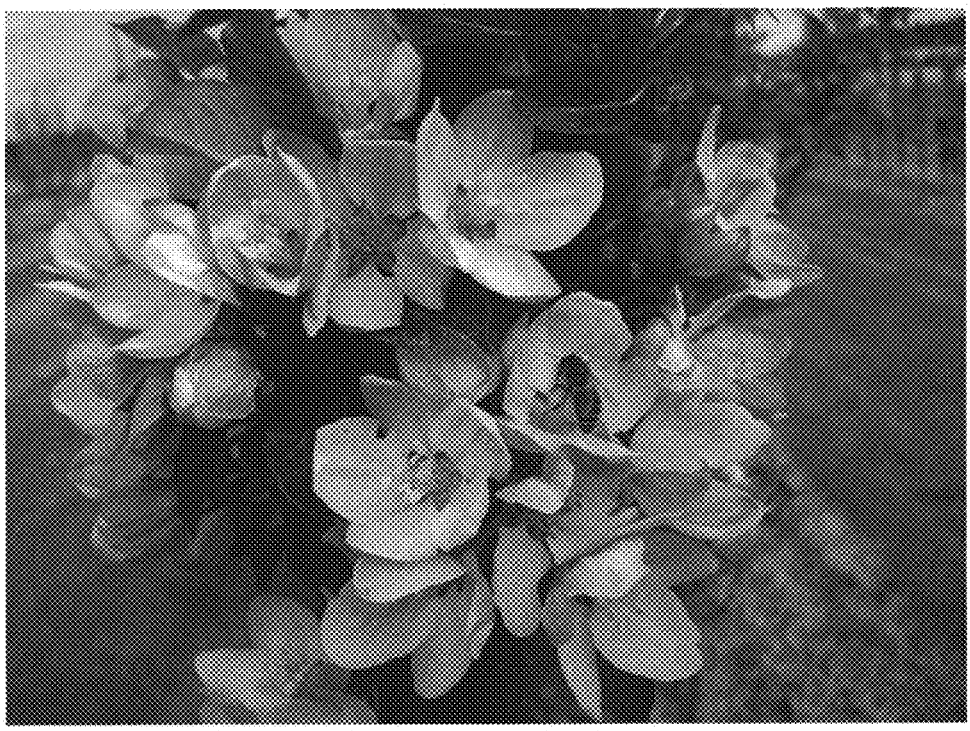
FIG. 6 illustrates details of blossoms of the new variety at full blossoming time
Figure 7:
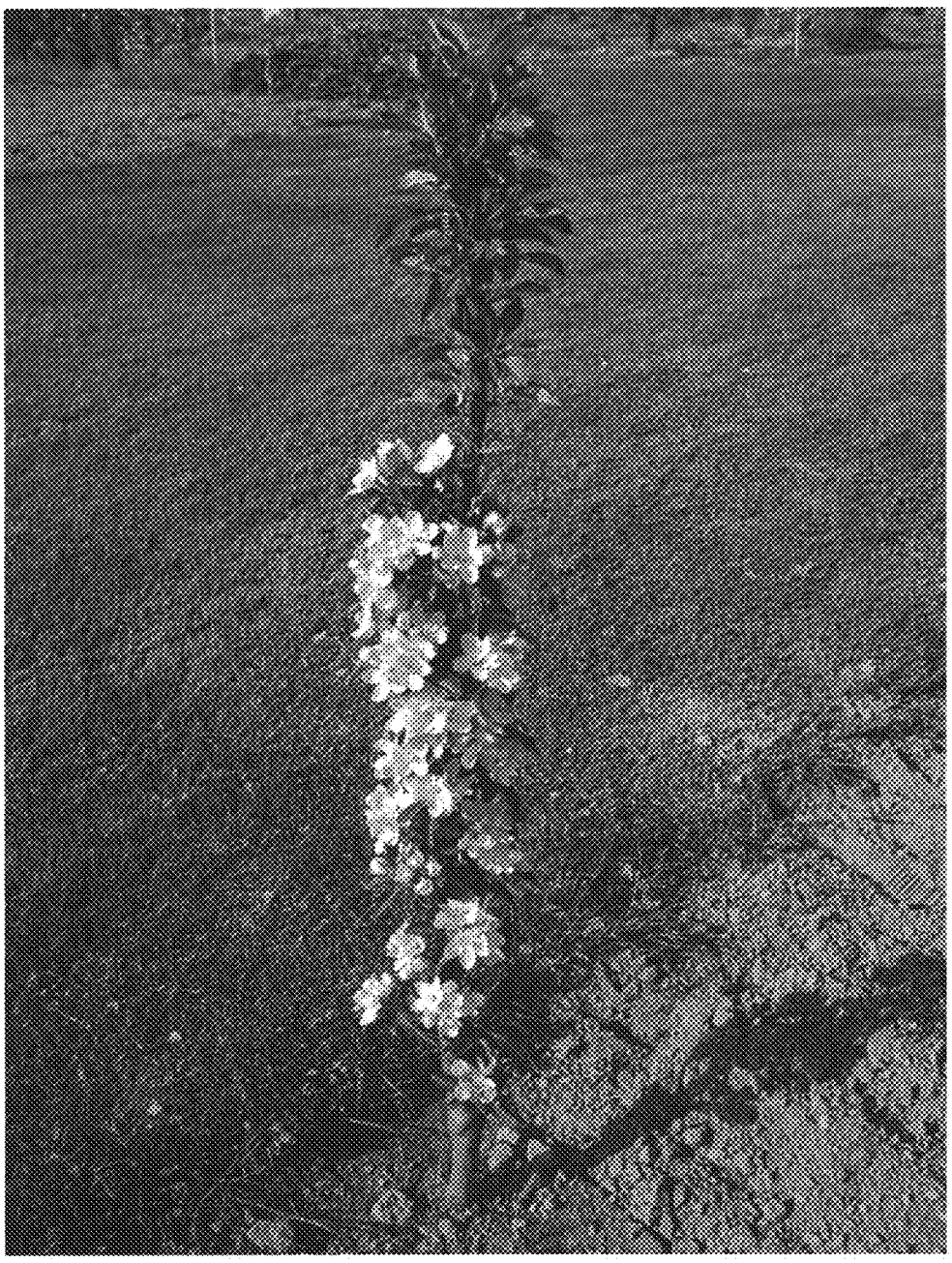
FIG. 7 illustrates a young, flowering tree grafted on MM 106 rootstock after 3 years from grafting.
Figure 8:
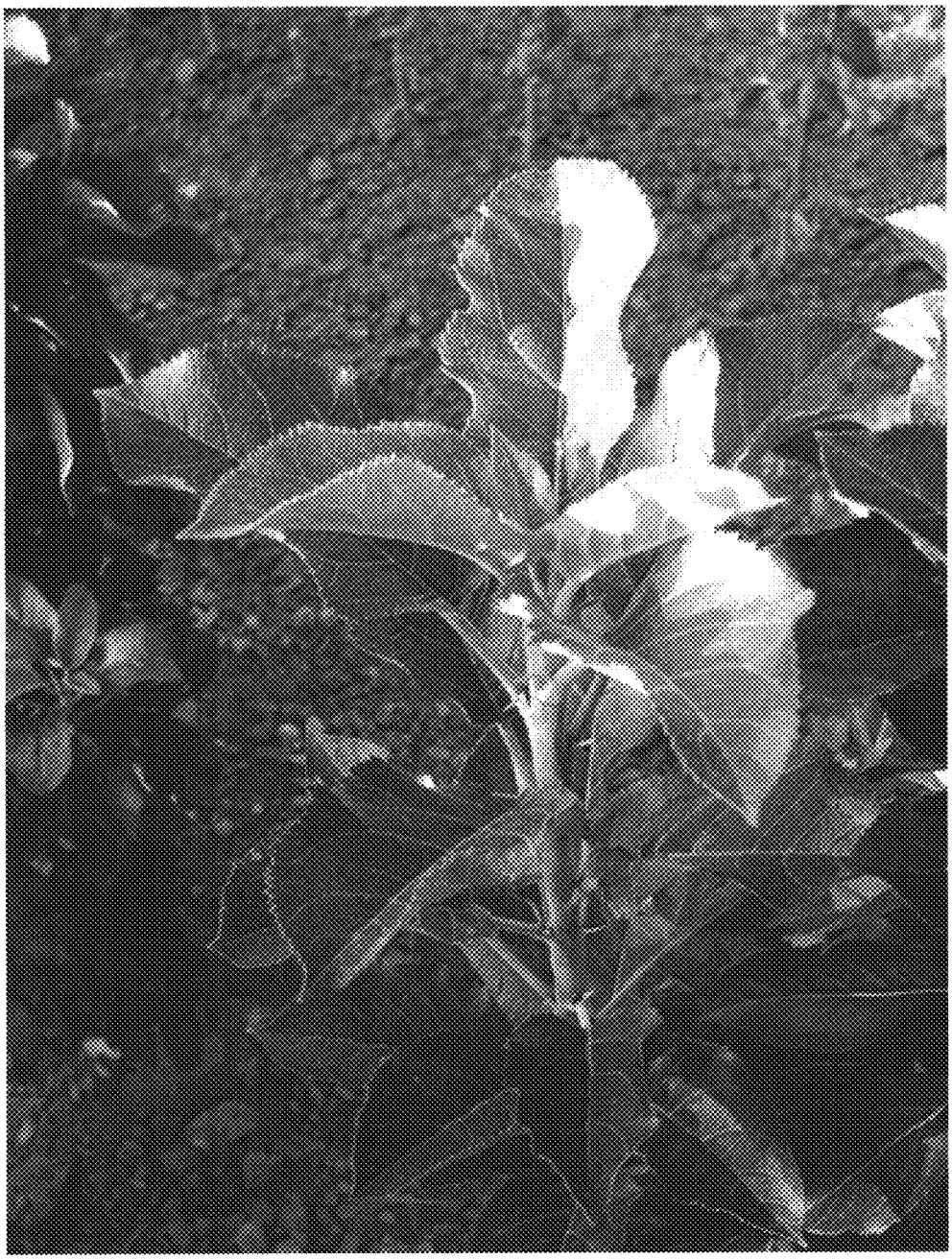
FIG. 8 illustrates a growing shoot of the new variety.
Figure 9:
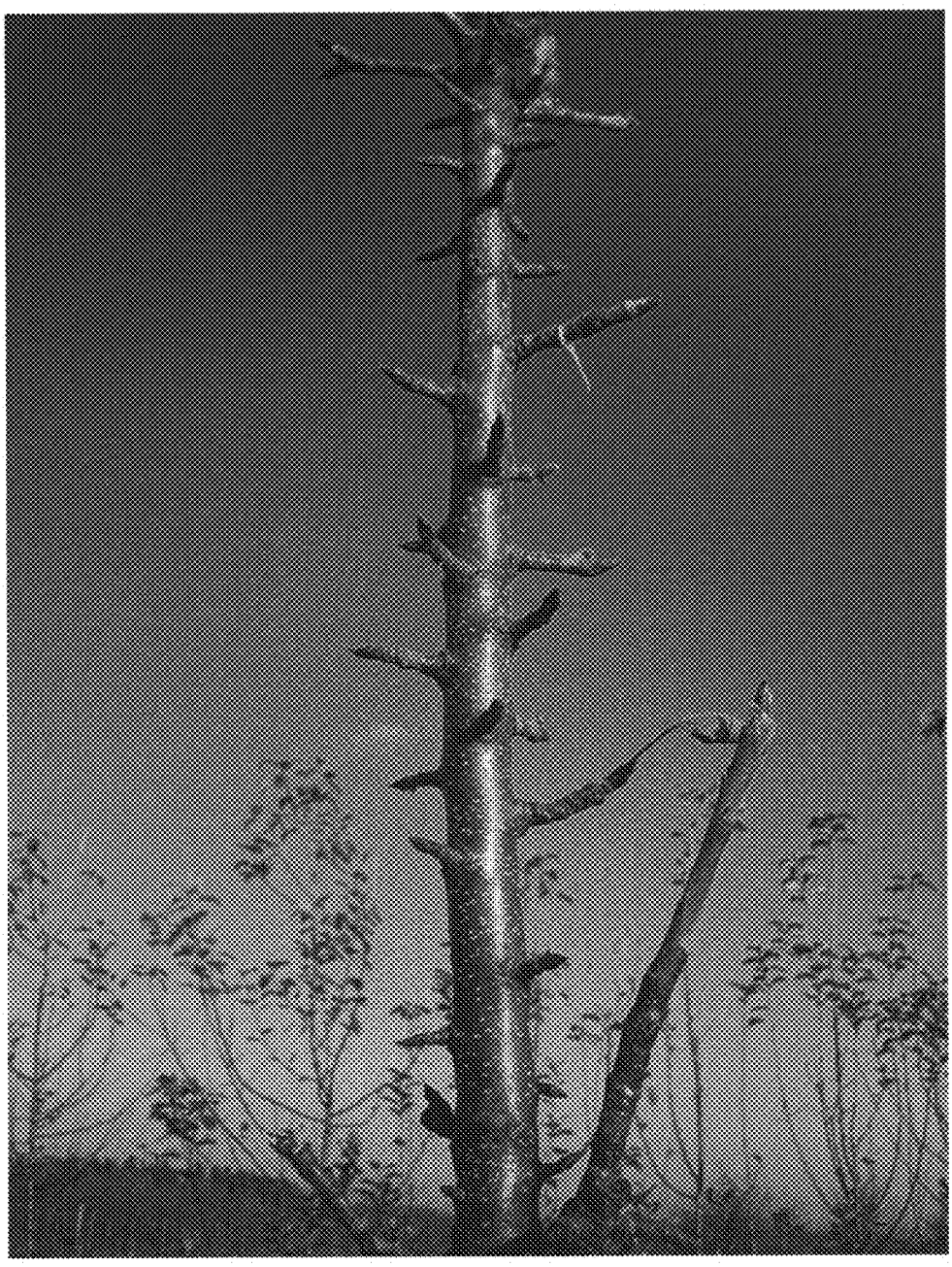
FIG. 9 illustrates the narrow, columnar tree growth form of the new variety with its many fruiting spurs.
Figure 10:
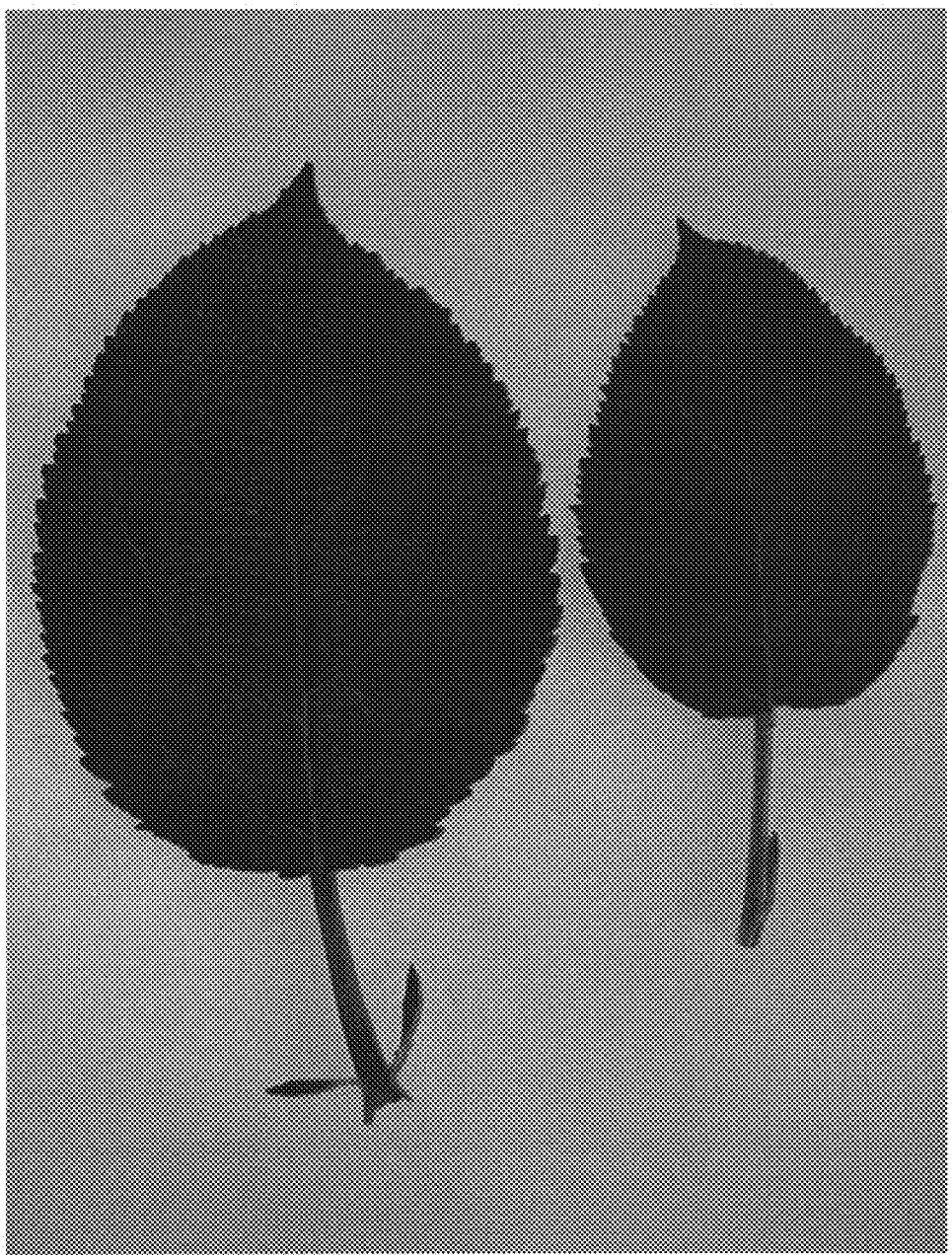
FIG. 10 illustrates a close-up view of a mature leaf and a young leaf of the new variety.

The following detailed description sets forth characteristics of the new cultivar. The new variety was grown under natural field conditions in The Czech Republic. The following fertilizer combination was used (Kg/ha/year): 55 parts nitrogen, 25 parts phosphorous, 60 parts potassium, 55 parts calcium, and 5 parts magnesium. Color references are primarily to The 1986 R.H.S. Colour Chart of The Royal Horticultural Society of London (in association with the Flower Council of Holland), Second Edition, and were identified under natural light.

TREE

Age: Approximately 9 years.
Size: Crown height of 3.4 m, width of 0.4 m.
Vigor: Moderate.
Density: Very compact.
Form: Erect and columnar.
Production: Moderate.
Growth type: Columnar.
Bearing: Annual; slightly alternate; predominantly on spurs.
Average productivity: 5 kg per 5-year old tree (grafted on MM 106 rootstock).

Trunk:
- *Size*.—Approximately 10.0 cm in diameter at 30.0 cm from the soil line.
- *Surface texture*.—Smooth, becoming slightly rough.
- *Bark color*.—Greyed-Orange Group RHS 177B.
- *Lenticels* (150.0 *cm above ground*).—Length: 2.0 mm to 4.0 mm. Width: 0.5 mm to 1.0 mm. Color: Greyed-Orange Group RHS 177B. Density: Variable, with 6 to 8 lenticels on average per 1 $cm^2$.

Branches: Not applicable — absent. The variety lacks a conventional branching system along the tree trunk.

Leaves (measured at the middle of growing shoot):
- *Length*.—About 80.0 mm to about 100.0 mm, averaging 86.0 mm.
- *Width*.—About 50.0 mm to about 60.0 mm, averaging about 56.0 mm.
- *Form*.—Oval to elliptic.
- *Texture*.—Smooth.
- *Thickness*.—Medium.
- *Base*.—Rounded and mostly symmetric.
- *Apex*.—Acute.
- *Margin*.—Biserrate.
- *Pubescence*.—Upper surface: None present. Lower surface: Very fine.
- *Color*.—Young leaves: Upper surface: Yellow-Green Group RHS 144A. Lower surface: Yellow-Green Group RHS 147C. Mature leaves: Upper surface: Yellow-Green Group RHS 147A. Lower surface: Yellow-Green Group RHS 147C.
- *Petiole*.—Shape: Straight, thickened and flattened at the base. Length: About 30.0 mm to 44.0 mm, averaging about 37.0 mm. Diameter: About 2.0 mm to 3.0 mm in the middle. Color: Yellow-Green Group RHS 146D, with Red-Purple Group RHS 59A to 59B near the base.
- *Stipule*.—Length: 1.1 cm. Shape: Elongated, with an acute apex. Color: Yellow-Green Group RHS 144A.
- *Veins*.—Venation type: Net-like, medium dense. Color: Upper surface: Yellow-Green Group RHS 144B. Lower surface: Green Group RHS 143D.

Flower buds:
- *Pedicel*.—Length: Typically in the range of 11.0 mm to 15.0 mm, with an average of 13.0 mm. Diameter: 1.6 mm on average. Color: Predominantly Yellow-Green Group RHS 144A.
- *Bud*.—Length: 18.5 mm on average. Width: 13.0 mm on average. Color: Red-Purple Group RHS 63A.

Flowers:
- *Bloom timing*.—At the end of April (April $30^{th}$, on average) — about 3-4 days before 'Golden Delicious'.
- *Pollination requirements*.—Diploid, self-sterile, needs pollinators such as *Malus* (crab apple) 'Evereste' (unpatented).
- *Number of flowers per cluster*.—5, rarely 6.
- *Average flower diameter*.—About 49.0 mm (44.0 mm to 52.7 mm).
- *Fragrance*.—Faint.
- *Petals*.—Number: 5. Length: 23.0 mm on average. Width: 14.0 mm on average. Shape: Ovate. Apex: Obtuse. Base: Rounded. Aspect: Positioned mostly touching. Margin: Entire. Texture and appearance: Soft and smooth. Color: When opening: Upper surface: Red-Purple Group RHS 65D and 63B. Lower surface: Red-Purple Group RHS 65D and 63C. Fully opened: Upper surface: Red-Purple Group RHS 70D and White Group RHS 155D. Lower surface: Red-Purple Group RHS 70C and White Group RHS 155D.
- *Sepals*.—Number: 5 (average). Shape: Long-conical; pointed. Margin: Entire. Texture: Finely pubescent. Length: Average of 9.0 mm from the union. Width: 4.0 mm at the base, 3.0 mm in the middle. Color: Upper surface: Yellow-Green Group RHS 144A, with a Red-Purple Group RHS 59A apex. Lower surface: Yellow-Green Group RHS 144B, with a Red-Purple Group RHS 59B apex.
- *Stamens*.—Number (per flower): 19 to 20. Filament length: 6.0 mm to 11.0 mm.
- *Anthers*.—Shape: Oval. Length: 2.5 mm. Color: Yellow Group RHS 10B.
- *Pollen*.—Color: Yellow Group RHS 12B. Amount (generally): Medium to high.

*Pistils*.—Length: 15.0 mm on average.

*Style*.—Length: 10.0 mm on average. Color: Yellow-Green Group RHS 145A.

*Stigma*.—Shape: Rounded. Color: Yellow-Green Group RHS 151B.

Fruit:

*Maturity when described*.—Eating maturity after two months in common storage.

*Date of picking*.—October of 2017.

*Size*.—Axial diameter: Predominantly about 56.0 mm. Transverse diameter: Predominantly about 78.0 mm.

*Weight per fruit*.—Average of 181 g (from 140 g to 225 g).

*Form*.—Obloid.

*Cavity*.—Description: Funnel-shaped, free of russet. Depth: Average of 12.0 mm. Breadth: Average of 36.0 mm.

*Basin*.—Description: Saucer-shaped. Depth: Average of 7.0 mm. Width: Average of 31.0 mm.

*Calyx*.—Persistent with semi-erect lobes.

Skin:

*Thickness*.—Thin to medium.

*Texture*.—Smooth, free of russet.

*Tendency to crack*.—Absent.

*Color*.—Overcolor of Red Group RHS 45A with a medium to large area of 46A.

*Ground color*.—Yellow Group RHS 5C.

Flesh:

*Aroma*.—Medium.

*Color*.—Yellow Group RHS 4D.

*Texture*.—Finely grained, with medium firmness.

*Eating quality*.—Good to very good, with a slightly sour taste.

Core:

*Bundle area*.—Onion-shaped on longitudinal section, locules closed to slightly open on cross section, having weakly distinct vascular strands.

*Calyx tube*.—Short.

*Depth of tube to shoulder*.—About 9.0 mm.

*Styles*.—Persistent as dry residues, closed with calyx lobes.

*Stamens*.—Persistent as dry residues, closed with calyx lobes.

*Seed cells*.—Wall: Smooth. Depth: 12.0 mm. Breadth: 8.0 mm on cross section. Longitudinal section: About 19.0 mm (length of seed cell).

Seeds:

*Number perfect*.—8 to 10.

*Number in one cell*.—1 to 2.

*Length*.—9.0 mm.

*Breadth*.—4.0 mm.

*Form*.—Long conical with an acute tip.

*Color*.—Greyed-Orange Group RHS 166A.

Stem:

*Length*.—15.0 mm on average.

*Width*.—2.3 mm on average.

*Color*.—Yellow-Green Group RHS 148A to 148B.

Use: As a late ripening, dessert apple variety having a columnar tree growth type and a very narrow growth habit with fruits of good eating quality and long storability that can be used for home or commercial apple growing for dessert or juice purposes.

Shipping quality: Average.

Keeping quality: Very good — about five to six months in common storage.

Tree winter hardiness: No frost damage observed at the place of origin, lowest winter temperatures approximately −20° C.

Bud winter hardiness: No frost damage observed at the place of origin, lowest winter temperatures approximately −20° C.

Drought tolerance: Unknown.

Disease resistance: $V_f$-resistance against scab.

I claim:

1. A new and distinct variety of *Malus domestica* (Borkh.) apple tree plant substantially as is herein described and illustrated.

* * * * *